United States Patent [19]

Ishii et al.

[11] Patent Number: 4,678,603
[45] Date of Patent: Jul. 7, 1987

[54] COLOGNE COMPOSITION

[75] Inventors: Hiroshi Ishii, Yokohama; Bunichiro Hosoda, Tokyo, both of Japan

[73] Assignee: Takasago Perfumery Co., Ltd., Tokyo, Japan

[21] Appl. No.: 836,502

[22] Filed: Mar. 5, 1986

[51] Int. Cl.$^4$ .......................... A61K 7/46; C11B 9/00
[52] U.S. Cl. .............................................. 252/522 R
[58] Field of Search .................................... 252/522 R

[56] References Cited

FOREIGN PATENT DOCUMENTS 0022440 7/1970 Japan .............................. 252/522 R
0047611 4/1980 Japan .............................. 252/522 R

*Primary Examiner*—Werren B. Lone
*Attorney, Agent, or Firm*—Cushman, Darby & Cushman

[57] ABSTRACT

A cologne composition such as eau de cologne which is characterized in comprising grape wine having a reduced acidity for example of pH 5.0 to 6.0. The grape wine may be included in the cologne composition in an amount of 10 to 35% by weight based on the whole composition.

3 Claims, No Drawings

COLOGNE COMPOSITION

BACKGROUND OF THE INVENTION (a) Technical Field of the Invention

This invention relates to a cologne composition such as eau de cologne or eau de toilette, and more particularly to a cologne composition containing wine for improving odor, skin feeling and etc.

(b) Description of the Prior Art

Cologne such as eau de cologne generally comprises as main components perfume, water and ethanol (or modified ethanol.

Ethanol included as a main component in colognes has various effects such as astringency, cleansing effect, sterilization and solubility. Such an ethanol (or modified ethanol) as useful for colognes is generally produced by a fermentation method or a synthetic method. Consequently, such an ethanol generally has a peculiar odor and burning taste according to the differences in raw material.

Therefore, in order to remove an pungent odor of ethanol, a modified alcohol which can be obtained by the distillation of a fruit wine or by utilizing a residue left from the production of an essential oil of jasmine, rose or lavender is also utilized as a solvent in a perfume or eau de cologne. However, the raw materials for such a modified alcohol production is limited in quantity and too expensive, and therefore the production of such a modified alcohol is undesirable in an industrial view point.

In view of above, the inventors have proposed a modified alcohol for fragrance or cosmetics, which is manufactured by contacting ethanol with a fermentation residue of grape fruit, which is obtained as a by-product from a grape wine manufacturing process thereby to produce an extract, and then refining the extract (Japanese Patent Application No. 58-182494: Japanese Patent Disclosure (Kokai) No. 60-75426). This modified alcohol is highly effective in eliminating the pungent odor of ethanol, has a good conformity with a perfume oil, and is low in the manufacturing cost.

These prior colognes including eau de cologne are traditionally manufactured to include a perfume of citrus type in addition to ethanol and water. Recently however, consumer's demands for fancy in perfume has been diversified, so that there have been posed new problems such as beautifying effects on skin, or an inclination for natural products.

SUMMARY OF THE INVENTION

The present invention has been made under the circumstances and has it object to provide a cologne such as eau de cologne, which is capable of giving a wetting feeling or a humidifying effect to the skin, and is rich in natural properties.

According to this invention, there is provided a cologne composition comprising alcohols, perfume oil and grape wine having a reduced acidity.

The inventors have noticed after a profound study with a view of meeting the consumer's demands as mentioned above that the peculiar flavor of grape wine comes not only from the perfume components included therein, but also from monosaccharide, oligosaccharide, various amino acids and peptide included in the grape wine, and that these compounds give a favorable effect to the skin.

Based on these findings, grape wine is now utilized according to this invention as a component of cologne after it is adjusted of its acidity.

DETAILED DESCRIPTION OF THE INVENTION

In this invention, cologne is defined to include various kinds of colognes, such for example as eau de cologne (perfume oil content: 5 to 8%), eau de toilette (perfume oil content: 7 to 10%), perfume cologne (perfume oil content: 10 to 12%), and shower cologne or body lotion (perfume oil content: 2 to 3%). The cologne composition according to this invention may contain alcohols at a concentration of 65 to 85%. It is also possible to add 2 to 3% by weight of sorbitol or glycerin in the cologne composition in order to improve its application feeling to the skin.

There is no limitation as to the kinds of grape wine to be employed as raw material according to this invention.

For example, any of commercially available wines, such as white wine, rose wine or red wine may be suitably employed.

It is however preferable to employ grape wine of higher purity. These grape wines can not be used as it is, because the acidity of these wines generally ranges from pH 2.8 to pH 3.6, which is too high and undesirable to be included as it is as a component of cologne.

The optimum acidity of cologne is generally 5.0 to 6.0 (pH), and therefore grape wine is required to be pretreated to adjust the acidity thereof to pH 5.0 to 6.0, the exact value thereof being dependent on the kind of perfume oil to be actually employed.

This adjustment of acidity of grape wine may be carried out in various ways. However, if alkali salts such as sodium carbonate, sodium bicarbonate and potassium carbonate are employed in neutralizing the grape wine, it will cause undesirable phenomena such as a generation of turbidity during the storage of the grape wine thus treated. The employment of calcium salts such as calcium carbonate have been found desirable in neutralizing the grape wine.

When a calcium salt is added to the grape wine, a precipitate of a calcium compound is produced.

Therefore if all of the precipitate of the calcium compound is removed by a filtering method after rendering the calcium compound to sufficiently precipitate, a transparent grape wine having an optimum acidity (hereinafter referred to as refined grape wine) can be obtained.

The amount of calcium carbonate to be required in neutralizing the grape wine would be about 10 to 25 g per 1 l of the grape wine, the exact amount thereof being dependent on the amount of saccharides included in the grape wine to be treated.

The refined grape wine obtained in this manner generally contains alcohols in a concentration of 10 to 15%. The cologne composition of this invention may comprise 10 to 35% by weight of the refined grape wine, 2 to 12% by weight of perfume oil and the balance of ethanol or isopropyl alcohol which meets a prescribed standard for cosmetics raw material.

Since a grape wine having a reduced acidity is employed as a component of cologne composition according to this invention, various components included in the grape wine, such as monosaccharide, oligosaccharide, amino acids and peptide will contribute to give a wetting feeling or a humidifying effect to the skin, thereby beautifying the skin and improving the feeling of the cologne to the skin.

Furthermore, the peculiar fermentation flavor of the grape wine will mask the pungent odor of ethanol, and exhibit a good conformity with a perfume oil, giving a sweet smell.

When rose wine or red wine is employed for manufacturing the refined grape wine, anthocyanin dyestuff included in these wines functions as a sunscreen agent, thereby inhibiting the color fading and denaturing of the perfume oil, and preventing the perfume oil from burning.

In the conventional method of manufacturing colognes (i.e. colognes containing no refined grape wine), a maturing period of more than three months at a temperature of less than 10° C. is required after mixing the components. In contrast to this, according to this invention, a maturing period of only less than 10 days is required after mixing the refined grape wine. Therefore, the manufacturing period of cologne according to this invention can be remarkably reduced thereby to increase the production efficiency, i.e. demonstrating an industrial advantage of this invention.

EXAMPLES

The invention will be understood more readily be reference to the following examples; however, these examples are intended to illustrate the invention and are not to be construed to limit the scope of the invention.

Following Producing Examples 1 to 3 explain manufacturing method of the refined grape wine employed for the colognes of this invention.

PRODUCING EXAMPLE 1

To 200 ml of Edel Wein Rose (a product of Edel Wein Co.) was gradually added calcium carbonate at the room temperature and under stirring to adjust the pH value of the wine.

When a total amount of 4.2 g of the calcium carbonate was added to the wine (the initial pH=3.1; light orange color), the acidity of the wine was reduced to pH 5.7 and the color of the wine changed to dark orange. Subsequently, floating substances were removed by using a filter (No. 5 B, a trade mark: a product of Toyo Roshi Co., Japan) to obtain a refined grape wine (Rose).

PRODUCING EXAMPLE 2

In almost the same manner as in Producing Example 1, Reserve vin Rouge (red: a product of Suntory Ltd., Japan) was treated to obtain a refined grape wine (Red).

In this case, when a total amount of 2.8 g of calcium carbonate was added to the wind (the initial pH: 3.5; red color), the acidity of the wine was reduced to pH 5.5, and the color thereof changed to deep purple.

PRODUCING EXAMPLE 3

In almost the same manner as in Producing Example 1, Ste. Neige Generic (White: Kyowa Hakko Kogyo Co. Ltd., Japan) was treated to obtain a refined grape wine (White).

In this case, when a total amount of 4.0 g of calcium carbonate was added to the wine (the initial pH=3.0; amber color), the acidity of the wine was reduced to pH 5.6, and the color thereof changed to dark yellow. Each of Rose, Red and White refined grape wines obtained in Producing Examples 1 to 3 was employed for manufacturing examples of colognes as shown in Table 1 to 3.

On the other hand, comparative examples containing no refined grape wine were also produced as shown in Table 1 to 3.

EXAMPLES 1 TO 6; COMPARATIVE EXAMPLES A AND B

Each of Examples 1 to 3 were manufactured by mixing Brucine-Denatured Alcohols, each of refined grape wines employed each of rose, red and white wines obtained by the said Producing Examples 1 to 3 as materials, and perfume oil Citrus FG (a product of Takasago Perfumery Co., Ltd.), according to Table 1 mentioned below, after standing the mixture at a temperature of about 10° C. in a dark room for four days and filtering the mixture through a filter paper to obtain body lotion.

While, Comparative Example a was manufactured in the same manner as mentioned above, except employing water as a substitute for the refined grape wine of this invention to obtain body lotion.

And Examples 4 to 6 were manufactured in the same manner as Examples 1 to 3, except employing Fragrance-Rolina-FG (a product of Takasago Perfumery Co., Ltd.) as perfume oil to obtain body lotion.

Further, Comparative Example b was manufactured in the same manner as Examples 4 to 6, except employing water as a substitute for the refined grape wine of this invention to obtain body lotion.

TABLE 1

|  | (Body lotion) | | | | | | | |
|---|---|---|---|---|---|---|---|---|
|  | Example: | | | | | | | |
|  | 1 | 2 | 3 | / | 4 | 5 | 6 | / |
|  | | | | Comparative Example: | | | | |
|  | / | / | / | a | / | / | / | b |
| Type of Refined Grape Wine | Rose | Red | White | — | Rose | Red | White | — |
| Brucine-Denatured Alcohols | 68 g | 68 g | 68 g | 72 g | 68 g | 68 g | 68 g | 72 g |
| Refined Grape Wine | 30 g | 30 g | 30 g | — | 30 g | 30 g | 30 g | — |
| Water | — | — | — | 26 g | — | — | — | 26 g |
| Perfume Oil Citrus FG (Product of Takasago Perfumery Co. Ltd.) | 2 g | 2 g | 2 g | 2 g | — | — | — | — |
| Perfume Oil Fragrance-Lorina-FG (Product of Takasago Perfumery Co. Ltd.) | — | — | — | — | 2 g | 2 g | 2 g | 2 g |

Each of the products of Examples 1 to 3 had a moderate sweet fragrance and a matured flavor without accompaniment of pungent odor of alcohols in top notes as was felt in the Comparative Example a.

Further, when each of Examples 1 to 3 was applied on the skin, it gave a humidifying feeling to the skin.

Each of the products of Examples 4 to 6 had, in contrast to Comparative Example b, a well-mellowed and rich feeling without accompaniment of pungent odor of alcohols. Further, when the products of Examples 4 to 6 were applied on the skin, they gave a humidifying and smooth feeling to the skin.

EXAMPLES 7 TO 9; COMPARATIVE EXAMPLES C AND D

Each of Examples 7 to 9 were manufactured by mixing Brucine-Denatured Alcohols, each of refined grape wines employed each of rose, red and white wines obtained by the said Producing Examples 1 to 3 as materials, and perfume oil Citrus FG (a product of Takasago Perfumery Co., Ltd.), according to Table 2 mentioned below, after standing the mixture at a temperature of about 10° C. in a dark room for four days and filtering the mixture through a filter paper to obtain eau de cologne.

While, Comparative Example c was manufactured in the same manner as mentioned above, except employing water as a substitute for the refined grape wine of this invention to obtain eau de cologne.

And Examples 10 to 12 were manufactured in the same manner as Examples 7 to 9, except employing Fragrance-Rolina-FG (a product of Takasago Perfumery Co., Ltd.) as perfume oil to obtain eau de cologne.

Further, Comparative Example d was manufactured in the same manner as Examples 10 to 12, except employing water as a substitute for the refined grape wine of this invention to obtain eau de cologne.

EXAMPLES 13 TO 18; COMPARATIVE EXAMPLES E AND F

Each of Examples 13 to 15 were manufactured by mixing Brucine-Denatured Alcohols, each of refined grape wines employed each of rose, red and white wines obtained by the said Producing Examples 1 to 3 as materials, and perfume oil Citrus FG (a product of Takasago Perfumery Co., Ltd.), according to Table 3 mentioned below, after standing the mixture at a temperature of about 10° C. in a dark room for four days and filtering the mixture through a filter paper to obtain eau de toilette.

While, Comparative Example e was manufactured in the same manner as mentioned above, except employing water as a substitute for the refined grape wine of this invention to obtain eau de toilette.

And Examples 16 to 18 were manufactured in the same manner as Examples 13 to 15, except employing Fragrance-Rolina-FG (a product of Takasago Perfumery Co., Ltd.) as perfume oil to obtain eau de toilette.

Further, Comparative Example f was manufactured in the same manner as Examples 16 to 18, except employing water as a substitute for the refined grape wine of this invention to obtain eau de toilette.

TABLE 2

| | (Eau de cologne) | | | | | | | |
|---|---|---|---|---|---|---|---|---|
| | Example: | | | | | | | |
| | 7 | 8 | 9 | / | 10 | 11 | 12 | / |
| | | | | Comparative Example: | | | | |
| | / | / | / | c | / | / | / | d |
| Type of Refined Grape Wine | Rose | Red | White | — | Rose | Red | White | — |
| Brucine-Denatured Alcohols | 72 g | 72 g | 72 g | 75 g | 72 g | 72 g | 72 g | 75 g |
| Refined Grape Wine | 23 g | 23 g | 23 g | — | 23 g | 23 g | 23 g | — |
| Water | — | — | — | 20 g | — | — | — | 20 g |
| Perfume Oil Citrus FG (Product of Takasago Perfumery Co. Ltd.) | 5 g | 5 g | 5 g | 5 g | — | — | — | — |
| Perfume Oil Fragrance-Rolina-FG (Product of Takasago Perfumery Co. Ltd.) | — | — | — | — | 5 g | 5 g | 5 g | 5 g |

TABLE 3

| | (Eau de toilette) | | | | | | | |
|---|---|---|---|---|---|---|---|---|
| | Example: | | | | | | | |
| | 13 | 14 | 15 | / | 16 | 17 | 18 | / |
| | | | | Comparative Example: | | | | |
| | / | / | / | e | / | / | / | f |
| Type of Refined Grape Wine | Rose | Red | White | — | Rose | Red | White | — |
| Brucine-Denatured Alcohols | 80 g | 80 g | 80 g | 82 g | 80 g | 80 g | 80 g | 82 g |
| Refined Grape Wine | 13 g | 13 g | 13 g | — | 13 g | 13 g | 13 g | — |
| Water | — | — | — | 11 g | — | — | — | 11 g |
| Perfume Oil Citrus FG (Product of Takasago Perfumery Co. Ltd.) | 7 g | 7 g | 7 g | 7 g | — | — | — | — |
| Perfume Oil Fragrance-Rolina-FG (Product of Takasago Perfumery Co. Ltd.) | — | — | — | — | 7 g | 7 g | 7 g | 7 g |

The products of each of Examples 7 to 9 had a moderate sweet fragrance and a matured flavor without accompaniment of pungent odor of alcohols in top notes as was felt in the Comparative Example c. Furthermore, when the products of Examples 7 to 9 were applied on the skin, they gave a humidifying feeling to the skin.

On the other hand, in contrast to Comparative Example d, the products of Examples 10 to 12 also has a well-mellowed and rich feeling without accompaniment of pungent odor of alcohols.

The products of Comparative Examples e and f containing no refined grape wine gave a feeling of dryness to the skin. In contrast to these, the products of Examples 13 to 15 and 16 to 18 gave a spreading, humidifying and smooth feeling to the skin when they were applied on the skin. Each Examples 13 to 15 and 16 to 18 had almost the same sweet fragrance as in the cases of each Examples 1 to 3 and 4 to 6.

What is claimed is:

1. A cologne composition comprising 10 to 35% by weight of refined grape wine having pH of 5 to 6 which is obtained by treating unrefined grape wine with 10 to 25 grams of calcium carbonate per one liter of said unrefined grape wine.

2. A cologne composition according to claim 1, which further includes 2 to 12% by weight (based on the whole composition) of perfume oil and the remainder of said composition being alcohols.

3. A cologne composition comprising:
   10 to 35% by weight of refined grape wine having pH of 5 to 6 which is obtained by treating unrefined grape wine with calcium carbonate;
   2 to 12% by weight of perfume oil; and
   the remainder of said composition being alcohols.

* * * * *